United States Patent
Gabant et al.

(10) Patent No.: US 7,022,892 B1
(45) Date of Patent: Apr. 4, 2006

(54) NON-HUMAN GENETICALLY MODIFIED MAMMAL LACKING THE ALPHA-FETOPROTEIN

(75) Inventors: Philippe Gabant, Brussels (BE); Josiane Roscam-Szpirer, Waterloo (BE)

(73) Assignee: Universite Libre de Bruxelles, Brussels (BE)

( * ) Notice: Subject to any disclaimer, the term of this patent is extended or adjusted under 35 U.S.C. 154(b) by 97 days.

(21) Appl. No.: 10/031,021

(22) PCT Filed: Jul. 11, 2000

(86) PCT No.: PCT/BE00/00081

§ 371 (c)(1), (2), (4) Date: Mar. 19, 2002

(87) PCT Pub. No.: WO01/03501

PCT Pub. Date: Jan. 18, 2001

Related U.S. Application Data (60) Provisional application No. 60/143,269, filed on Jul. 12, 1999.

(51) Int. Cl.
G01N 33/00 (2006.01)
A01K 67/00 (2006.01)
A01K 67/027 (2006.01)

(52) U.S. Cl. .................... 800/3; 800/8; 800/9; 800/13; 800/18

(58) Field of Classification Search .................... 800/2, 800/4; 514/44
See application file for complete search history.

(56) References Cited

FOREIGN PATENT DOCUMENTS

| WO | WO 95/23862 | 9/1995 |
|---|---|---|
| WO | WO 96/22787 | 8/1996 |
| WO | WO 99/09150 | 2/1999 |
| WO | WO 00/40693 | 7/2000 |
| WO | WO 00/53759 | 9/2000 |

OTHER PUBLICATIONS

Houdebine (J. of Biotechnology 98, 145-160, 2002).*
Polejaeva et al. (Theriogenology, vol. 53, pp. 117-126, 2000.*
Sigmund, Thromb Basc Biol., 2000, 20:1425-2429.*
Bampton, Brain Res, 841, pp. 123-134, 1999.*
Rulicke et al., Experimental Physiology, 85, 6:589-601, 20000.*
Jin, et al. (1998) α-Fetoprotein gene sequences mediating Afr2 regulation during liver regeneration. Proc. Natl. Acad. Sci. USA, 95:8767-8772.
Cirillo, et al. (1995) Developmental Regulation of α-Fetroprotein Expression in Intestinal Epithelial Cells of Transgenic Mice. Developmental Biology 168:395-405.
Tyner, et al. (1990) The Ontogency of α-fetoprotein Gene Expression in the Mouse Gastrointestinal Tract. J. Cell Biology 110:915-927.
Millonig, et al., (1995) Molecular Analysis of the Distal Enhancer of the Mouse α-Fetoprotein Gene. Molecular and Cellular Biology p. 3848-3856.
Chen, et al. (1999) Identification of a Cis-Acting Element in the Rat α-Fetoprotein Gene and its Specific Binding proteins in F9 cells During Retinoic Acid-Induced Differentiation. J. Cellular Biochemistry 72:25-34.
Butterfield, et al. (1999) Generation of Human T-cell Responses to an HLA-A2.1-restricted Peptide Epitope Derived from α-Fetoprotein. Cancer Research 59:3134-3142.
Henriette, et al. (1997) Negative Regulation of the α-Fetoprotein Gene in Fibroblasts: Identification and Characterization of cis and trans Elements. *Folia Biologica* (Praha) 43:5-13.
Young, et al. (1982) Construction and Expression in vivo of an Internally Deleted mouse α-Fetoprotein gene: Prescence of a Transcribed Alu-like repeat within the First Intervening Sequence. Nucleic Acids Research 10:3099-3116.
Scohy, et al. (2000) Identification of an Enhancer and an Alternative Promoter in the First Intron of the α-Fetoprotein gene. Nucleic Acids Research 28(19)3743-3751.
Askew, et al. 1993. Site-directed point mutations in embryonic stem cells: A gene-targeting tag-and-exchange strategy. *Molecular and Cellular Biology*,13(7):4115-4124.
Bradley, et al. 1998. Thirteen years of manipulating the mouse genome: A personal history. *Int. J. Dev. Biol.*, 42: 943-950.

(Continued)

*Primary Examiner*—Janet Epps-Ford
(74) *Attorney, Agent, or Firm*—Knobbe, Martens, Olson & Bear, L.L.P.

(57) ABSTRACT

The present invention is related to a non-human genetically modified mammal comprising a mutation, a partial or total deletion of the genetic sequence encoding the wild type mammal alpha-fetoprotein.

3 Claims, 5 Drawing Sheets

OTHER PUBLICATIONS

Eiferman, et al. 1981. Intragenic amplification and divergence in the mouse α-fetoprotein gene. *Nature*, 294:713-718.

Gorin, et al. 1980. Structure of the α-fetoprotein gene in the mouse. *Proc. Natl. Acad. Sci.*, 77(3):1351-1355.

Hasty, et al. 1991. The length of homology required for gene targeting in embryonic stem cells. *Molecular and Cellular Biology*, 11(11):5586-5591.

Hasty, et al. 1991. Target frequency and integration pattern for insertion and replacement vectors in embryonic stem cells. *Molecular and Cellular Biology*, 11(9):4509-4517.

Law, et al. 1981. Homology between the primary structure of a α-fetoprotein, deduced from a complete cDNA sequence, and serum albumin. *Nature*, 291:201-205.

Rubinstein, et al. 1993. Introduction of a point mutation into the mouse genome by homologous recombination in embryonic stem cells using a replacement type vector with a selectable marker. *Nucleic Acids Research*, 21(11):2613-2617.

Valancius, et al. 1991. Testing an "in-out" targeting procedure for making subtle genomic modifications in mouse embryonic stem cells. *Molecular and Cellular Biology*, 11(3):1402-1408.

* cited by examiner

Afp Genetic Sequence

```
tcccacttcc agcactgcct gcggtgaagg aacaagcagc catgaagtgg atcacacccg
cttccctcat cctcctgcta catttcgctg cgtccaaagc attgcacgaa aatgagtttg
ggatagcttc cacgttagat tcctcccagt gcgtgacgga gaagaatgtg cttagcatag
ctaccatcac ctttacccag tttgttccgg aagccaccga ggaggaagtg aacaaaatga
ctagcgatgt gttggctgca atgaagaaaa actctggcga tgggtgttta gaaagccagc
tatctgtgtt tctggatgaa atttgccatg agacggaact ctctaacaag tatggactct
caggctgctg cagccaaagt ggagtggaaa gacatcagtg tctgctggca cgcaagaaga
ctgctccggc ctctgtccca cccttccagt ttccagaacc tgccgagagt tgcaaagcac
atgaagaaaa cagggcagtg ttcatgaaca ggttcatcta tgaagtgtca aggaggaacc
ccttcatgta tgccccagcc attctgtcct tggctgctca gtacgacaag gtcgttctgg
catgctgcaa agctgacaac aaggaggagt gcttccagac aaagagagca tccattgcaa
aggaattaag agaaggaagc atgttaaatg agcatgtatg ttcagtgata agaaaatttg
gatcccgaaa cctccaggca acaaccatta ttaagctaag tcaaaagtta actgaagcaa
attttactga gattcagaag ctggccctgg atgtggctca catccacgag gagtgttgcc
aaggaaactc gctggagtgt ctgcaggatg gggaaaaagt catgacatat atatgttctc
aacaaaatat tctgtcaagc aaaatagcag agtgctgcaa attacccatg atccaactag
gcttctgcat aattcacgca gagaatggcg tcaaacctga aggcttatct ctaaatccaa
gccagttttt gggagacaga aattttgccc aatttcttc agaggaaaaa atcatgttca
tggcaagctt tcttcatgaa tactcaagaa ctcaccccaa ccttcctgtc tcagtcattc
taagaattgc taaaacgtac caggaaatat tggagaagtg ttcccagtct ggaaatctac
ctggatgtca ggacaatctg gaagaagaat tgcagaaaca catcgaggag agccaggcac
tgtccaagca aagctgcgct ctctaccaga ccttaggaga ctacaaatta caaaatctgt
tccttattgg ttacacgagg aaagcccctc agctgacctc agcagagctg atcgacctca
ccgggaagat ggtgagcatt gcctccacgt gctgccagct cagcgaggag aaatggtccg
gctgtggtga gggaatggcc gacattttca ttggacattt gtgtataagg aatgaagcaa
gccctgtgaa ctctggtatc agccactgct gcaactcttc gtattccaac aggaggctat
gcatcaccag ttttctgagg gatgaaacct atgcccctcc cccattctct gaggataaat
tcatcttcca caaggatctg tgccaagctc agggcaaagc cctacagacc atgaaacaag
agcttctcat taacctggtg aagcaaaagc ctgaactgac agaggagcag ctggcggctg
tcactgcaga tttctcgggc cttttggaga agtgctgcaa agcccaggac caggaagtct
gtttcacaga agagggtcca aagttgattt ccaaaactcg tgatgctttg ggcgtttaaa
catctccaga aggaagagtg gacaaaaaaa tgtgttgacg ctttggtgtg agccttttgg
cttaactgta actgctagta ctttaaccac atggtgaaga tgtccatgtg agatttctat
accttaggaa taaaaacttt tcaactatt
```
(SEQ ID NO: 7)

```
MKWITPASLILLLHFAASKALHENEFGIASTLDSSQCVTEKNVLSIATITFTQFVPEATEEEVNKMTSDVLAAMKKNSGD
GCLESQLSVFLDEICHETELSNKYGLSGCCSQSGVERHQCLLARKKTAPASVPPFQFPEPAESCKAHEENRAVFMNRFIY
EVSRRNPFMYAPAILSLAAQYDKVVLACCKADNKEECFQTKRASIAKELREGSMLNEHVCSVIRKFGSRNLQATTIIKLS
QKLTEANFTEIQKLALDVAHIHEECCQGNSLECLQDGEKVMTYICSQQNILSSKIAECCKLPMIQLGFCIIHAENGVKPE
GLSLNPSQFLGDRNFAQFSSEEKIMFMASFLHEYSRTHPNLPVSVILRIAKTYQEILEKCSQSGNLPGCQDNLEEELQKH
IEESQALSKQSCALYQTLGDYKLQNLFLIGYTRKAPQLTSAELIDLTGKMVSIASTCCQLSEEKWSGCGEGMADIFIGHL
CIRNEASPVNSGISHCCNSSYSNRRLCITSFLRDETYAPPPFSEDKFIFHKDLCQAQGKALQTMKQELLINLVKQKPELT
EEQLAAVTADFSGLLEKCCKAQDQEVCFTEEGPKLISKTRDALGV
```
(SEQ ID NO: 8)

*FIG. 5*

NON-HUMAN GENETICALLY MODIFIED MAMMAL LACKING THE ALPHA-FETOPROTEIN

CROSS-REFERENCE TO RELATED APPLICATIONS

This is the U.S. National Phase under 35 U.S.C. § 371 of International Application No. PCT/BE00/00081, filed Jul. 11, 2000, which claims priority to U.S. Provisional Application No. 60/143,269, filed Jul. 12, 1999.

FIELD OF THE INVENTION

The present invention is related to a non-human genetically modified mammal, preferably a knock-out mouse, comprising a partial or total deletion of a genetic sequence encoding the alpha-fetoprotein (AFP) and used as a model for the study of fertilization or contraceptive methods and drugs.

The present invention is related to a non-human mammalian pluripotential embryonic stem cell comprising a partial or total deletion of a genetic sequence encoding a mammal alpha-fetoprotein (AFP).

The present invention is also related to study, testing and/or screening method and device of known or unknown compounds able to bind the mammal alpha-fetoprotein (AFP) and that may be used as agonist or antagonist of oestrogens to the mammal alpha-fetoprotein.

BACKGROUND OF THE INVENTION

Alpha-fetoprotein (AFP) is a glycoprotein present in the serum and a classical oncofetal marker. This protein is expressed at high levels during fetal life in the liver and the visceral endoderm of the yolk sac, and at lower levels in the developing gastrointestinal tract (Andrews et al., 1982; Tilghman and Belayew 1982), in the adult serum only trace amount are detected (Tilghman and Belayew 1982). The protein expressed by the embryos is secreted and present in the maternal blood circulation during gestation, the level of AFP concentration in the maternal serum is use to detect fetuses with spina bifida or Down's syndrome. The reason for this altered AFP level associated with those pathologies are not understood, but they have been used extensively in prenatal screening. The synthesis of AFP decreases dramatically after birth and only trace amounts are detected in adult liver. However expression of afp is associated with hepatocarcinomas and liver regeneration induced by partial hepatectomy or acute tetrachloride (CC14) intoxication. The control of afp gene expression has thus attracted much attention and it has been shown that afp expression is regulated by transcriptional mechanisms involving a large promoter and three distant enhancers (review of Chen et al. (1997)). Because AFP is synthesized during the G1 and S phases, it has been hypothesized that intracellular AFP affects cell growth (Leffert and Sell, 1974; Sell et al., 1975; Tsukada and Hirai, 1975; Belanger et al., 1978). The observation that AFP is able to bind estrogen led to the suggestion that AFP plays a role in the control of cell metabolism. In addition to binding estrogen, AFP, like albumin to which it is evolutionary related, is able to bind other steroids and endogenous and exogenous substances such as fatty acids, billirubin and various pharmaceutical agents suggesting that AFP may play a general transportation function. For the fetus, in this respect, AFP could serve as a modulator/modifier of various cell growth regulatory pathways during embryonic and fetal development in vertebrates by interacting and/or binding cytoplasmic chaperone proteins that normally escort nuclear receptors or transcription co-factors through the cytoplasm towards organelle interfaces (Mizejewski, 1995, 1985). AFP has also been proposed to protect the embryo against the maternal immune system, on the basis of the observation that addition of purified AFP into the culture of splenic or lymphnode mononuclear cells exerts a suppressive effect on antibody synthesis.

The different hypotheses proposed for AFP function(s) can be focused on the fetal life (stage at which the gene is strongly transcripted) since the protein is described as a fetoprotein.

At the present time, no document of the state of the art has suggested that the alpha-fetoprotein may play an essential role for female reproduction and fertility.

Aims of the Invention

The present invention aim to provide new models (animal models) as well as new methods and devices for the study, the testing and/or the screening of fertility or contraception methods, compounds and compositions intended for adult mammals (including humans) and/or for the study, the testing and/or the screening of new methods, compounds or compositions intended for the treatment and/or the prevention of osteoporosis.

SUMMARY OF THE INVENTION

The present invention is related to a non-human genetically modified mammal (preferably a knock-out mouse) comprising a mutation, a partial or total deletion in a genetic sequence encoding a mammal alpha-fetoprotein (AFP) described in GenBank (v00743).

Advantageously, said mammal comprises an heterozygous or homozygous mutation, partial or total deletion in the genetic sequence encoding a mammal AFP.

According to another embodiment of the present invention, said mammal is a sterile female comprising said homozygous mutation, partial or total deletion.

The present invention is also related to specific sequences such as primers that are used to identify if a mammal comprises said mutation, partial or total deletion heterozygously or homozygously.

Another aspect of the present invention is related to a non-human mammal pluripotential embryonic stem cell, preferably a mouse pluripotential embryonic stem cell comprising a partial or total deletion of a genetic sequence encoding a mammal AFP. Said stem cell can be advantageously used to obtain the non-human genetically modified mammal according to the invention by methods well known by the person skilled in the art described hereafter.

A further aspect of the present invention is related to the use of the non-human mammal according to the invention for the study, the testing and/or the screening of known or unknown anti-osteoporosis fertility and/or contraceptive methods, compounds or compositions.

A last aspect of the present invention is related to study, testing and/or screening methods and devices comprising the AFP or a portion of said AFP, preferably the AFP domain III comprising about 200 amino acids (as described by Festin (1999)), being fixed upon a solid support and used as a substrate for known or unknown compounds or compositions in a competitive test or method. Said device comprises also a medium comprising (possibly labeled) oestrogens. The device according to the invention can be a chromatographic column upon which the AFP or the portion thereof is fixed or a study, testing and/or screening kit comprising disposed separately the various media necessary for said study, testing and/or screening.

According to a preferred embodiment of the present invention, said device or kit may comprise a cell having integrated an oestrogen-sensitive (proloactine) promoter gene whose activation may result from the fixation of known or unknown compounds or compositions upon the AFP. Said known or unknown compound or composition could be used advantageously as an agonist of an oestrogen.

The present invention is also related to this unknown agonist or antagonist of oestrogens screened and identified by the method and the device according to the invention. This unknown molecule finds an application in the field of fertility and/or contraceptive methods and compositions and/or is used also for the treatment and/or the prevention of osteoporosis.

BRIEF DESCRIPTION OF THE DRAWINGS

This patent or application file contains at least one drawing executed in color. Copies of this patent or application publication with colored drawings will be provided by the Office upon request and payment of the necessary fees. FIGS. 3 to 6 are executed in color.

FIGS. 3A to 3H illustrate expression of the lacZ gene in embryonic and adult tissue. FIGS. 3A, 3G and 3H illustrate expression in adult liver and gut cells.

FIGS. 3B to 3F illustrate expression of the lacZ gene in embryonic tissues.

FIG. 5A illustrates the nucleotide sequence of the afp gene. FIG. 5B illustrates the amino acid sequence of the afp protein.

DETAILED DESCRIPTION OF THE PRESENT INVENTION

Generation of Mice Carrying a Germ-Line Mutation in the Afp Gene

A clone containing a 129 genomic fragment of AFP loci was isolated from a lambda library. The library was screened with a probe containing the mouse afp promoter. The genomic insert of about 16 kb was subcloned into pKIL-PCR2 (Gabant et al., 1997). The targeting vector (pAFP K.O-1), consists of two recombination arms. The 5' arms (2.5 kb) were generated by polymerase chain reaction (PCR) using the following primers: N-Mer1: agagcggccgcggaagt-gacaaagcagaacc (SEQ ID NO: 1) annealing to the MerIse-quence of the afp enhancer 1 (Godboute et al. (1988)) and a primer of the X-exon1: agactcgagggatgagggaagcgggtgtg (SEQ ID NO: 2) complementary to the afp exon1. The PCR fragment generated using Pfu polymerase (Stratagene) was cloned in the pCR-blunt vector (Invitrogen).

The 3' arms were subcloned from the lambda into pBSI-IKS+ vector (Stratagene). The 5' recombination arm was introduced upstream the 3' recombination arm. The IRES lacZ/neo reporter-selective cassette was introduced between these recombination arms. The tk2 negative selective marker was introduced into the SalI site to generate pAFP KO-1. This construction was linearized with NotI and electroporated into E14 ES cells. Correctly targeted clones were identified by Southern blot analysis using an external probe from the 5' region.

ES Cell Injections and Animal Genotyping

Recombinant ES cells carrying the targeted allele were injected in C57BL/6J blastocysts. Animals were genotyped by extraction of DNA from tails.

RNA Isolation, Northern Blot Analysis

Total RNA was isolated using Trizol (Gibco BRL) extraction according to the manufacturer instructions. For the Northern analysis 20 μg of total RNA were electrophoresed and transferred to nylon membranes as described. Filters were then hybridized.

Western Blot Analysis

Proteins were separated by SDS-PAGE using 7.5% polyacrylamide gels in a Bio-Rad Mini Protean gel chamber and blotted onto Nitrocellulose filters in a Bio-Rad Trans Blot chamber according to the manufacturer's instructions. Proteins were detected using anti-AFP, anti-Albumin; anti Beta-galactosidase serum (ICN Biochemicals) the signal was detected with ECL detection system (Amersham).

LacZ Reporter Gene Expression

To isolate embryonic stages, natural matings were set up and presence of a vaginal plug at noon the following day was taken as 0.5 days of gestation. Staged embryos were stained with X-Gal as wholemounts as described by Forrester et al. (1996). For cryostat sectioning, tissues were embedded in optimal cutting temperature (OTC) compounds (Miles, Inc., Elkart, Ind.), and sections stained for X-Gal were counterstained with haematoxylin and eosin, and mounted.

Targeted Mutagenesis of the afp Gene

Figure 1:
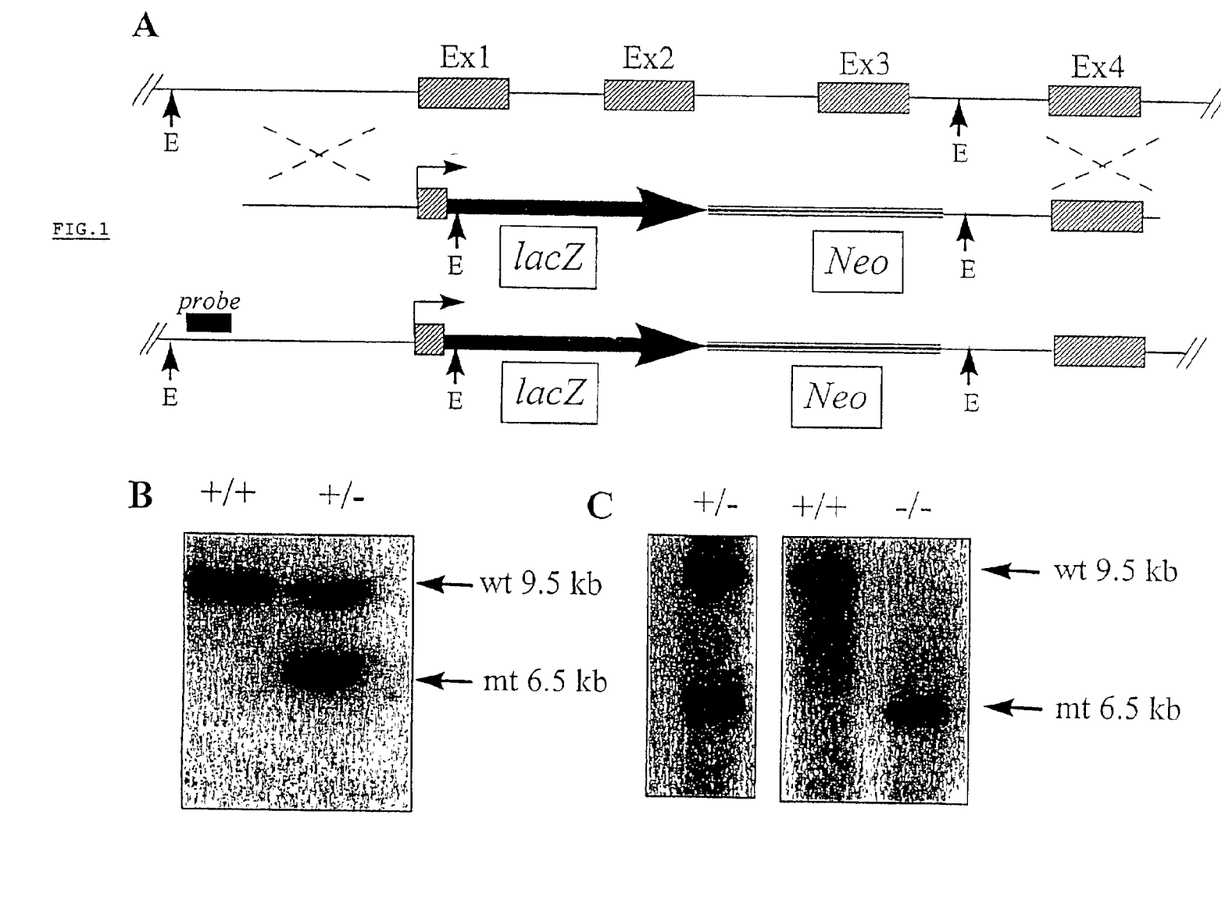
FIG. 1A illustrates the targeted disruption of the afp gene to generate alleles which are deleted for most of the sequence of exon 1, for exon 2 and for exon 3.
FIG. 1B illustrates the detection of homologous insertion by Southern blot analysis.
FIG. 1C illustrates a Southern blot analysis of the progeny of homozygous (−/−) chimeric animals.

The afp gene was disrupted by gene targeting in embryonic stem (ES) cells. The lacZ reporter was introduced in afp gene by homologous recombination and placed under the control of the AFP promoter-enhancer region. The resulting allele is deleted for most of the sequence of exon1, for exon2 and 3 (see FIG. 1A) and homologous insertion was detected by Southern analysis (see FIG. 1B). To test the functionality of the reporter one may take advantage of the observation that AFP is expressed in embryoid bodies (Abe et al., 1996). Reporter gene activity is highly turn on in some cells of these bodies (see FIG. 2A). No expression of the reporter was detected in undifferentiated ES cells grown in the presence of LIF.

ES cells afp lacZ1/+ were injected into C57BL/6J blastocysts. Chimeric animals were obtained and mated with outbred CD1 or inbred 129/CGR to test for germ line transmission. Phenotypically normal heterozygous mice afp lacZ1/+ were generated and detected by Southern blot (see FIG. 1C).

Reporter Expression Analysis

Figure 3:
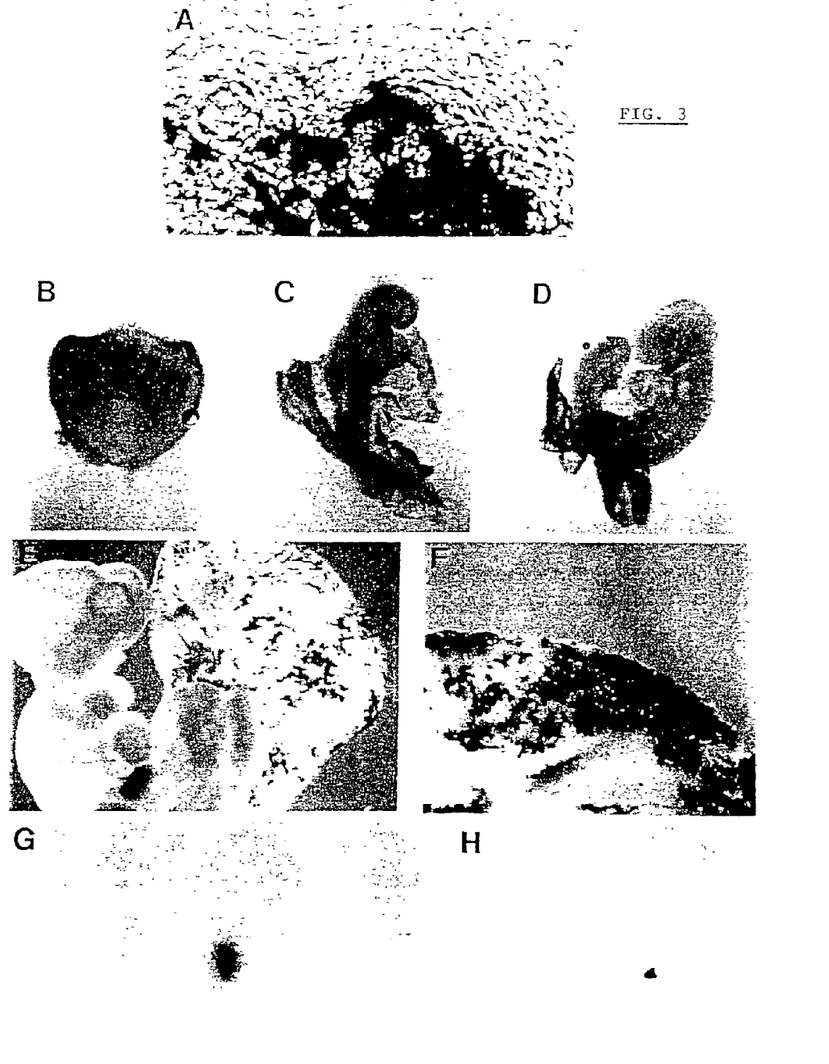

Expression of the lacZ reporter gene expression in embryonic and adult tissues was analyzed. As shown in FIG. 3 the β-galactosidase activity was detected in predicted embryonic tissues. In the visceral endoderm only patches of cells were observed to turn the reporter strongly on. In the adult tissues tested specific staining was only detected in cells of the liver and in cells of the gut.

Figure 2:
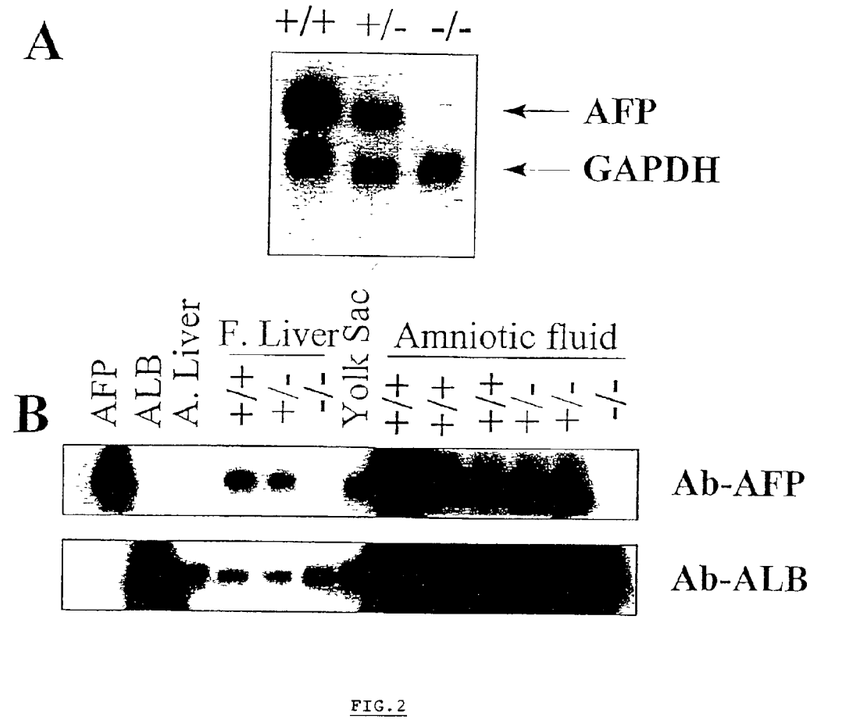
FIG. 2A is a Northern blot analysis of total RNA from embryonic liver.
FIG. 2B is a Western blot analysis of embryonic liver and amniotic fluid protein extracts.

Intercrosses of heterozygotes (afp lacZ1/+) gave rise to viable, apparently normal homozygous mutant mice at a Mendelian ratio in CD1 and C57/B16. On the other hand, a significant divergence was observed in the 129 background (Table 1). To determine whether the targeted allele indeed results in a null mutation, total RNA from the liver of embryos was analyzed by Northern blot hybridization (FIG. 2A). A strong signal at 2.2 kb corresponding to the afp transcript was detected in wild type and heterozygous embryos. No signal was detected in RNA samples extracted from homozygous embryonic liver, showing that the recombination disrupted the afp transcript in these animals. A Western blot was also performed on embryonic liver and amniotic fluid protein extracts (FIG. 2B) and a strong signal was detected with the wild type extracts while no band corresponding to the AFP was visible in the homozygous extracts demonstrating that these animals do not express AFP.

TABLE 1

| | Intercrosses | | | | |
| --- | --- | --- | --- | --- | --- |
| | Parents | | Offsprings | | |
| Strains | Male | Female | +/+ | +/− | −/− |
| CD1 | +/− | +/− | 108 | 258 | 102 |
| 129 | +/− | +/− | 34 | 48 | 13 |
| C57/black-6 | +/− | +/− | 19 | 43 | 19 |

AFP is Required for Female Fertility

The Mendelian ratio obtained in CD1 and C57/black-6 background demonstrates that there is no reduction in the intercrosses. On the other hand, the divergence observed in 129 background suggests that AFP is involved in the gestation and that its importance is only revealed in some genetic contexts. In these litters derived from intercrossing heterozygous animals, homozygous embryos develop in the presence of their wild type and heterozygote littermates. AFP produced by these embryos is secreted and present in the maternal serum. To determine whether afp lacZ1/lacZ1 mice are able to develop in the complete absence of AFP afp lacZ1/lacZ1 males and afp lacZ1/lacZ1 females were mated. No pups were obtained from these intercrosses suggesting an essential role of AFP for development and/or fertility (see Table 2). To test if fertility was affected, afp lacZ1/lacZ1 males and females were mated with wild type animals. Males homozygous for an afp disrupted allele appeared fertile and sired offspring but homozygous females never produce any live offspring. To test if natural matings occur with the afp lacZ1/lacZ1 females leave with wild type males the vaginal plug were checked. No plugs were detected with those females, showing that the origin of the observed infertility is due to an absence of mating. To identify the defect underlying the reproductive capacity of homozygous females, the reproductive system of those animals was analyzed. The reproductive system of the afp lacZ1/lacZ1 females was dissected and at this stage of the analysis appeared complete A major anatomical difference is notable between ovaries from afp lacZ1/lacZ1 and afp +/+: the ovaries of afp lacZ1/lacZ1 are smooth, this observation suggests that those females do not ovulate. Histological analysis of mature afp lacZ1/lacZ1 ovaries shown that their homozygous tissues do not contain corpus lutea, the lack of these structure is indicative of the absence of ovulation (see FIG. 4). The afp lacZ1/lacZ1 ovaries contain follicles at the different stages of maturation, this suggests that the default of AFP during the development has no effect on the female gametogenesis. However, the presence of follicles does not prove that these gametes are competent for maturation. To test the competence of the afp lacZ1/lacZ1 follicles, they were dissected out and analyzed their potential of maturation in vitro. Complete maturation was obtained in vitro with the dissected oocytes from afp lacZ1/lacZ1 animals. Taken together these data indicates that those females do not ovulate properly and thus that a signal needed to trigger ovulation is absent in the afp lacZ1/lacZ1 mice.

TABLE 2

| Phenotypical analysis | | | | |
| --- | --- | --- | --- | --- |
| Parents | | Offsprings | | |
| Male | Female | +/+ | +/− | −/− |
| −/− | −/− (2) | 0 | 0 | 0 |
| −/− | +/+ (6) | 0 | 71 | 0 |
| +/+ | −/− (13) | 0 | 0 | 0 |

Table 2: Infertility phenotype of the afp$^{lacZ1/lacZ1}$ (−/−) homozygous animals were mated, no offsprings were obtained from these matings. To test fertility of the afp$^{lacZ1/lacZ1}$ (−/−) males and females, homozygous males and females were mated with wild type (+/+) animals. For the different breedings the number of mating is given in brackets.

It was also observed that afp$^{lacZ1/lacZ1}$ follicles are able to mature normally in vitro (data not shown) suggesting that the defect could be in a signal required to trigger ovulation and indeed ovulation can be induced in these animals by a superovulation protocol (Table 3).

TABLE 3

| Ovulation induction in afp$^{lacZ1/+}$ and afp$^{lacZ1/lacZ1}$ females | |
| --- | --- |
| Mice injected | Number of oocytes obtained |
| afp$^{lacZ1/+}$ females (9 weeks) | 37 |
| afp$^{lacZ1/lacZ1}$ females (9 weeks) | 31 |

Table 3: Induction of ovulation in afp$^{lacZ1/lacX1}$ females. afp$^{lacZ1/lacZ1}$ and afp$^{lacZ1/+}$ females were hormonally treated to induce ovulation. The average number of postovulation oocytes obtained from 6 individual females tested.

Mouse Genotyping by PCR

In order to identify a possible mutation or deletion in the afp gene, a specific genotyping of afp −/− mice by PCR has been developed. Two primers are used for the first afp#1 anneals in the afp promoter region (−116 bp to −137 bp: according to the +1 of the mouse afp gene). The second primer afp#2 is complementary to the first exon of the mouse afp gene (+141 bp to +160 bp: according to the +1 of the mouse afp gene): sequence deleted in the afp −/− knock-out mouse described in the text.

| Sequence afp#1: | ccctgctctgttaattattg (SEQ ID NO: 3) |
|---|---|
| Sequence afp#2: | gaaaatagctcccaagtcac (SEQ ID NO: 4) |

No amplification product (300 bp) was observed in afp −/− animals. This amplification is present in wild type and heterozygous mice.

To differentiate +/− from wild type, a second PCR is performed using two primers giving an amplification on the DNA introduced in the genome of the transgenic animals (this sequence is not present in wild type animals).

For the knock-out mouse for afp described in the text: a couple of primers complementary to lacZ (*E. coli* gene) can be used.

| lacZ#1: | acaacgtcgtgactgggaaaac (SEQ ID NO: 5) |
|---|---|
| lacZ#2: | taatgggataggttacgt (SEQ ID NO: 6) |

Those primers will only give a signal (287 bp) on +/− and no signal on wild type DNA samples.

The physiological role of the alpha-fetoprotein, the most abundant serum protein expressed by mammalian embryos remains to be establish. This protein related to albumin excreted by the embryos into the maternal blood circulation has attracted attention and due to its abundance it has been postulated that the presence of this protein was essential for embryonic development. To determine the function of AFP this gene was disrupted by homologous recombination in embryonic stem cells. Surprisingly homozygous afp$^{lacZ1/lacZ1}$ are viable showing that expression of AFP by the embryo itself is not require for normal and complete development. This phenotype shows that the structure of the homozygous females was generally maintained. The different stages of ovocytes maturation are founded in these ovaries and shown to accomplish their maturation in vitro. Ovulation was induced in these females by hormonal induction and ovocytes were produced. Although AFP is synthesized at a high level during fetal life (mainly by the liver and the visceral endoderm of the yolk sac), low level of AFP mRNA has been reported in different other fetal and adult tissues as well as in adult rats. However, the level of expression in such tissues is very low. Another explanation is that the ovulation in those females is affected by the lack of AFP during development.

The fact that in adults afp$^{lacZ1/lacZ1}$ ovulation can be induced argues for the absence in those females of a signal needed to trigger ovulation. This suggests that AFP is involved in the transportation of an element needed for ovulation in the adults.

By the disruption of the mouse AFP, one may show that fetal serum protein is required for females ovulation.

The fact that analbuminic rats are fertile shows that at least albumin cannot rescue AFP. This show that albumin and AFP plays two different role and that AFP is involved in the function of females ovaries.

Figure 4:
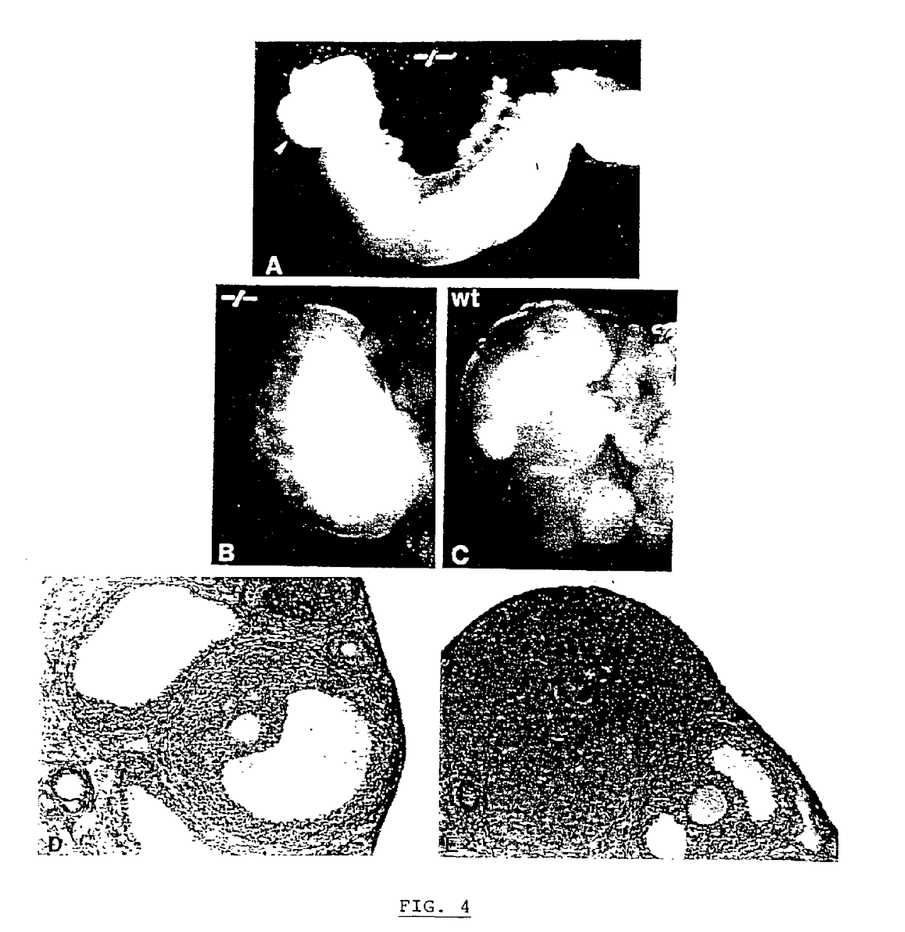
FIG. 4A illustrates the structure of the ovary (arrow) and uterus of an adult afplacZ1/lacZ1(−/−) female.
FIG. 4B illustrates the ovary from a 12 week old afplacZ1/lacZ1 animal.
FIG. 4C illustrates the ovary from a 12 week old mutated afplacZ1/lacZ1 female.
FIG. 4D illustrates the general histological structure of afplacZ1/lacZ ovaries.
FIG. 4E illustrates the structure of wild type ovaries at 4 months.

The specific phenotype of the non-human mammals according to the invention is also illustrated in the enclosed FIG. 4, which presents the anatomical and histological analysis for the afp$^{lacZ1/lacZ1}$ ovaries:

A: Structure of the ovary (arrow) and uterus of an adult afp$^{lacZ1/lacZ1}$ (−/−) female;
B: Ovary from 12 weeks old afp$^{lacZ1/lacZ1}$;
C: Ovary from a 12 weeks old wild type female: the surface distortions are due to the presence of large type follicles, whereas afp$^{lacZ1/lacZ1}$ ovaries are smooth;
D: The general histological structure of the afp$^{lacZ1/lacZ1}$ ovaries is not affected and mature Graafian follicles are present in those tissues (section from a fourth month old female);
E: At 4 months, the wild type ovaries exhibit large corpus lutea, indicative of successful ovulation. Those structures are never found in afp$^{lacZ1/lacZ1}$ ovaries.

Therefore, the non-human female mammals that present homozygously said mutation, partial or total deletion in the afp gene do not cycle. The surface of the ovaries is smooth and is not characterized by the presence of large follicles. Their histological structure is not generally affected, and Graafian follicles are identified in the tissues but no large corpus lutea is present.

Furthermore, females comprising an homozygous mutation or partial or total deletion in the afp gene do not allow uterus nidification of an embryo.

Additional experiments have shown that the afp gene is not essential for the survival of the mice. Indeed, as females give birth to severa animals, it was possible that the afp$^{−/+}$ may survive to brothers and sisters (afp$^{+/+}$ or afp$^{+/−}$) simultaneously present in the uterus of the female.

Therefore, in order to extrapolate the observed phenotype and genotype to the human population, the inventors have shown that blastocysts implanted one by one in pseudogravite females will obtain the birth of alive afp$^{−/−}$ animals that present the same phenotype as above-described (fertile males, sterile females).

Therefore, the afp$^{−/−}$ phenotype corresponds to alive sterile females, which is a phenotype that may exist in the mouse population as well as in the human population.

The invention claimed is:

1. A sterile female genetically modified mouse which does not undergo menstrual cyclization, wherein the genome of said mouse comprises a mutation, a partial deletion or a total deletion in each allele of endogenous genetic sequence encoding the wild type alpha-fetoprotein (AFP), wherein said mutation, partial deletion or total deletion results in loss of expression of a functional AFP in both alleles.

2. The sterile female genetically modified mouse of claim 1, wherein said sterile female genetically modified mouse is homozygous for a mutation, a partial deletion or a total deletion in endogenous genetic sequence encoding a functional alpha-fetoprotein (AFP).

3. A method for identifying an agent for use in increasing fertility, comprising:

obtaining a sterile female genetically modified mouse which does not undergo menstrual cyclization wherein the genome of said mouse comprises a mutation, a partial deletion or a total deletion in each allele of endogenous genetic sequence encoding the wild type alpha-fetoprotein (AFP), wherein said mutation, partial deletion or total deletion results in loss of expression of functional AFP in both alleles;

contacting said sterile female genetically modified mouse with said agent; and determining the effects of said agent on fertility in said sterile female genetically modified mouse.

* * * * *

SEQUENCE LISTING

<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: N-Mer1 primer

<400> SEQUENCE: 1
agagcggccg cggaagtgac aaagcagaac c                               31

```
<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: X-exon1
      primer

<400> SEQUENCE: 2
agactcgagg gatgagggaa gcgggtgtg                              29

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: afp#1
      primer

<400> SEQUENCE: 3
cccctgctct gttaattatt g                                      21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: afp#2
      primer

<400> SEQUENCE: 4
gaaaatagct cccaagtcac                                        20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: lacZ#1
      primer

<400> SEQUENCE: 5
acaacgtcgt gactgggaaa ac                                     22

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: lacZ#2
      primer

<400> SEQUENCE: 6
taatgggata ggttacgt                                          18

<210> SEQ ID NO 7
<211> LENGTH: 2009
<212> TYPE: DNA
<213> ORGANISM: Apodemus
<220> FEATURE:
<221> NAME/KEY: CDS
<222> LOCATION: (42)..(1856)
<223> OTHER INFORMATION:

<400> SEQUENCE: 7
tcccacttcc agcactgcct gcggtgaagg aacaagcagc c atg aag tgg atc aca   56
```

-continued

```
                        Met Lys Trp Ile Thr
                         1           5
ccc gct tcc ctc atc ctc ctg cta cat ttc gct gcg tcc aaa gca ttg    104
Pro Ala Ser Leu Ile Leu Leu Leu His Phe Ala Ala Ser Lys Ala Leu
             10              15              20 cac gaa aat gag ttt ggg ata gct tcc acg tta gat tcc tcc cag tgc    152
His Glu Asn Glu Phe Gly Ile Ala Ser Thr Leu Asp Ser Ser Gln Cys
         25              30              35 gtg acg gag aag aat gtg ctt agc ata gct acc atc acc ttt acc cag    200
Val Thr Glu Lys Asn Val Leu Ser Ile Ala Thr Ile Thr Phe Thr Gln
             40              45              50 ttt gtt ccg gaa gcc acc gag gag gaa gtg aac aaa atg act agc gat    248
Phe Val Pro Glu Ala Thr Glu Glu Glu Val Asn Lys Met Thr Ser Asp
         55              60              65 gtg ttg gct gca atg aag aaa aac tct ggc gat ggg tgt tta gaa agc    296
Val Leu Ala Ala Met Lys Lys Asn Ser Gly Asp Gly Cys Leu Glu Ser
70              75              80              85 cag cta tct gtg ttt ctg gat gaa att tgc cat gag acg gaa ctc tct    344
Gln Leu Ser Val Phe Leu Asp Glu Ile Cys His Glu Thr Glu Leu Ser
             90              95             100 aac aag tat gga ctc tca ggc tgc tgc agc caa agt gga gtg gaa aga    392
Asn Lys Tyr Gly Leu Ser Gly Cys Cys Ser Gln Ser Gly Val Glu Arg
        105             110             115 cat cag tgt ctg ctg gca cgc aag aag act gct ccg gcc tct gtc cca    440
His Gln Cys Leu Leu Ala Arg Lys Lys Thr Ala Pro Ala Ser Val Pro
        120             125             130 ccc ttc cag ttt cca gaa cct gcc gag agt tgc aaa gca cat gaa gaa    488
Pro Phe Gln Phe Pro Glu Pro Ala Glu Ser Cys Lys Ala His Glu Glu
        135             140             145 aac agg gca gtg ttc atg aac agg ttc atc tat gaa gtg tca agg agg    536
Asn Arg Ala Val Phe Met Asn Arg Phe Ile Tyr Glu Val Ser Arg Arg
150             155             160             165 aac ccc ttc atg tat gcc cca gcc att ctg tcc ttg gct gct cag tac    584
Asn Pro Phe Met Tyr Ala Pro Ala Ile Leu Ser Leu Ala Ala Gln Tyr
        170             175             180 gac aag gtc gtt ctg gca tgc tgc aaa gct gac aac aag gag gag tgc    632
Asp Lys Val Val Leu Ala Cys Cys Lys Ala Asp Asn Lys Glu Glu Cys
        185             190             195 ttc cag aca aag aga gca tcc att gca aag gaa tta aga gaa gga agc    680
Phe Gln Thr Lys Arg Ala Ser Ile Ala Lys Glu Leu Arg Glu Gly Ser
        200             205             210 atg tta aat gag cat gta tgt tca gtg ata aga aaa ttt gga tcc cga    728
Met Leu Asn Glu His Val Cys Ser Val Ile Arg Lys Phe Gly Ser Arg
    215             220             225 aac ctc cag gca aca acc att att aag cta agt caa aag tta act gaa    776
Asn Leu Gln Ala Thr Thr Ile Ile Lys Leu Ser Gln Lys Leu Thr Glu
230             235             240             245 gca aat ttt act gag att cag aag ctg gcc ctg gat gtg gct cac atc    824
Ala Asn Phe Thr Glu Ile Gln Lys Leu Ala Leu Asp Val Ala His Ile
            250             255             260 cac gag gag tgt tgc caa gga aac tcg ctg gag tgt ctg cag gat ggg    872
His Glu Glu Cys Cys Gln Gly Asn Ser Leu Glu Cys Leu Gln Asp Gly
        265             270             275 gaa aaa gtc atg aca tat ata tgt tct caa caa aat att ctg tca agc    920
Glu Lys Val Met Thr Tyr Ile Cys Ser Gln Gln Asn Ile Leu Ser Ser
        280             285             290 aaa ata gca gag tgc tgc aaa tta ccc atg atc caa cta ggc ttc tgc    968
Lys Ile Ala Glu Cys Cys Lys Leu Pro Met Ile Gln Leu Gly Phe Cys
295             300             305
```

-continued

| | | |
|---|---|---|
| ata att cac gca gag aat ggc gtc aaa cct gaa ggc tta tct cta aat<br>Ile Ile His Ala Glu Asn Gly Val Lys Pro Glu Gly Leu Ser Leu Asn<br>310                              315                          320                       325 | 1016 |
| cca agc cag ttt ttg gga gac aga aat ttt gcc caa ttt tct tca gag<br>Pro Ser Gln Phe Leu Gly Asp Arg Asn Phe Ala Gln Phe Ser Ser Glu<br>                        330                          335                        340 | 1064 |
| gaa aaa atc atg ttc atg gca agc ttt ctt cat gaa tac tca aga act<br>Glu Lys Ile Met Phe Met Ala Ser Phe Leu His Glu Tyr Ser Arg Thr<br>                  345                          350                        355 | 1112 |
| cac ccc aac ctt cct gtc tca gtc att cta aga att gct aaa acg tac<br>His Pro Asn Leu Pro Val Ser Val Ile Leu Arg Ile Ala Lys Thr Tyr<br>              360                          365                        370 | 1160 |
| cag gaa ata ttg gag aag tgt tcc cag tct gga aat cta cct gga tgt<br>Gln Glu Ile Leu Glu Lys Cys Ser Gln Ser Gly Asn Leu Pro Gly Cys<br>375                            380                          385 | 1208 |
| cag gac aat ctg gaa gaa gaa ttg cat aaa cac atc gag gag agc cag<br>Gln Asp Asn Leu Glu Glu Glu Leu His Lys His Ile Glu Glu Ser Gln<br>390                              395                        400                        405 | 1256 |
| gca ctg tcc aag caa agc tgc gct ctc tac cag acc tta gga gac tac<br>Ala Leu Ser Lys Gln Ser Cys Ala Leu Tyr Gln Thr Leu Gly Asp Tyr<br>                        410                          415                        420 | 1304 |
| aaa tta caa aat ctg ttc ctt att ggt tac acg agg aaa gcc cct cag<br>Lys Leu Gln Asn Leu Phe Leu Ile Gly Tyr Thr Arg Lys Ala Pro Gln<br>                        425                          430                        435 | 1352 |
| ctg acc tca gca gag ctg atc gac ctc acc ggg aag atg gtg agc att<br>Leu Thr Ser Ala Glu Leu Ile Asp Leu Thr Gly Lys Met Val Ser Ile<br>                  440                          445                        450 | 1400 |
| gcc tcc acg tgc tgc cag ctc agc gag gag aaa tgg tcc ggc tgt ggt<br>Ala Ser Thr Cys Cys Gln Leu Ser Glu Glu Lys Trp Ser Gly Cys Gly<br>              455                          460                        465 | 1448 |
| gag gga atg gcc gac att ttc att gga cat ttg tgt ata agg aat gaa<br>Glu Gly Met Ala Asp Ile Phe Ile Gly His Leu Cys Ile Arg Asn Glu<br>470                            475                        480                        485 | 1496 |
| gca agc cct gtg aac tct ggt atc agc cac tgc tgc aac tct tcg tat<br>Ala Ser Pro Val Asn Ser Gly Ile Ser His Cys Cys Asn Ser Ser Tyr<br>                        490                          495                        500 | 1544 |
| tcc aac agg agg cta tgc atc acc agt ttt ctg agg gat gaa acc tat<br>Ser Asn Arg Arg Leu Cys Ile Thr Ser Phe Leu Arg Asp Glu Thr Tyr<br>                  505                          510                        515 | 1592 |
| gcc cct ccc cca ttc tct gag gat aaa ttc atc ttc cac aag gat ctg<br>Ala Pro Pro Pro Phe Ser Glu Asp Lys Phe Ile Phe His Lys Asp Leu<br>              520                          525                        530 | 1640 |
| tgc caa gct cag ggc aaa gcc cta cag acc atg aaa caa gag ctt ctc<br>Cys Gln Ala Gln Gly Lys Ala Leu Gln Thr Met Lys Gln Glu Leu Leu<br>535                            540                          545 | 1688 |
| att aac ctg gtg aag caa aag cct gaa ctg aca gag gag cag ctg gcg<br>Ile Asn Leu Val Lys Gln Lys Pro Glu Leu Thr Glu Glu Gln Leu Ala<br>550                            555                        560                        565 | 1736 |
| gct gtc act gca gat ttc tcg ggc ctt ttg gag aag tgc tgc aaa gcc<br>Ala Val Thr Ala Asp Phe Ser Gly Leu Leu Glu Lys Cys Cys Lys Ala<br>                        570                          575                        580 | 1784 |
| cag gac cag gaa gtc tgt ttc aca gaa gag ggt cca aag ttg att tcc<br>Gln Asp Gln Glu Val Cys Phe Thr Glu Glu Gly Pro Lys Leu Ile Ser<br>                  585                          590                        595 | 1832 |
| aaa act cgt gat gct ttg ggc gtt taaacatctc cagaaggaag agtggacaaa<br>Lys Thr Arg Asp Ala Leu Gly Val<br>              600                          605 | 1886 |
| aaaatgtgtt gacgctttgg tgtgagcctt ttggcttaac tgtaactgct agtactttaa | 1946 |
| ccacatggtg aagatgtcca tgtgagattt ctataccttag gaataaaaa cttttcaact | 2006 | att                                                              2009

<210> SEQ ID NO 8
<211> LENGTH: 605
<212> TYPE: PRT
<213> ORGANISM: Apodemus

<400> SEQUENCE: 8

```
Met Lys Trp Ile Thr Pro Ala Ser Leu Ile Leu Leu Leu His Phe Ala
1               5                   10                  15

Ala Ser Lys Ala Leu His Glu Asn Glu Phe Gly Ile Ala Ser Thr Leu
            20                  25                  30

Asp Ser Ser Gln Cys Val Thr Glu Lys Asn Val Leu Ser Ile Ala Thr
        35                  40                  45

Ile Thr Phe Thr Gln Phe Val Pro Glu Ala Thr Glu Glu Val Asn
    50                  55                  60

Lys Met Thr Ser Asp Val Leu Ala Ala Met Lys Lys Asn Ser Gly Asp
65                  70                  75                  80

Gly Cys Leu Glu Ser Gln Leu Ser Val Phe Leu Asp Glu Ile Cys His
                85                  90                  95

Glu Thr Glu Leu Ser Asn Lys Tyr Gly Leu Ser Gly Cys Cys Ser Gln
            100                 105                 110

Ser Gly Val Glu Arg His Gln Cys Leu Leu Ala Arg Lys Lys Thr Ala
        115                 120                 125

Pro Ala Ser Val Pro Pro Phe Gln Phe Pro Pro Ala Glu Ser Cys
    130                 135                 140

Lys Ala His Glu Glu Asn Arg Ala Val Phe Met Asn Arg Phe Ile Tyr
145                 150                 155                 160

Glu Val Ser Arg Arg Asn Pro Phe Met Tyr Ala Pro Ala Ile Leu Ser
                165                 170                 175

Leu Ala Ala Gln Tyr Asp Lys Val Val Leu Ala Cys Cys Lys Ala Asp
            180                 185                 190

Asn Lys Glu Glu Cys Phe Gln Thr Lys Arg Ala Ser Ile Ala Lys Glu
        195                 200                 205

Leu Arg Glu Gly Ser Met Leu Asn Glu His Val Cys Ser Val Ile Arg
    210                 215                 220

Lys Phe Gly Ser Arg Asn Leu Gln Ala Thr Thr Ile Ile Lys Leu Ser
225                 230                 235                 240

Gln Lys Leu Thr Glu Ala Asn Phe Thr Glu Ile Gln Lys Leu Ala Leu
                245                 250                 255

Asp Val Ala His Ile His Glu Glu Cys Cys Gln Gly Asn Ser Leu Glu
            260                 265                 270

Cys Leu Gln Asp Gly Glu Lys Val Met Thr Tyr Ile Cys Ser Gln Gln
        275                 280                 285

Asn Ile Leu Ser Ser Lys Ile Ala Glu Cys Cys Lys Leu Pro Met Ile
    290                 295                 300

Gln Leu Gly Phe Cys Ile Ile His Ala Glu Asn Gly Val Lys Pro Glu
305                 310                 315                 320

Gly Leu Ser Leu Asn Pro Ser Gln Phe Leu Gly Asp Arg Asn Phe Ala
                325                 330                 335

Gln Phe Ser Ser Glu Glu Lys Ile Met Phe Met Ala Ser Phe Leu His
            340                 345                 350

Glu Tyr Ser Arg Thr His Pro Asn Leu Pro Val Ser Val Ile Leu Arg
        355                 360                 365
```

-continued

```
Ile Ala Lys Thr Tyr Gln Glu Ile Leu Glu Lys Cys Ser Gln Ser Gly
    370                 375                 380

Asn Leu Pro Gly Cys Gln Asp Asn Leu Glu Glu Glu Leu His Lys His
385                 390                 395                 400

Ile Glu Glu Ser Gln Ala Leu Ser Lys Gln Ser Cys Ala Leu Tyr Gln
                405                 410                 415

Thr Leu Gly Asp Tyr Lys Leu Gln Asn Leu Phe Leu Ile Gly Tyr Thr
            420                 425                 430

Arg Lys Ala Pro Gln Leu Thr Ser Ala Glu Leu Ile Asp Leu Thr Gly
        435                 440                 445

Lys Met Val Ser Ile Ala Ser Thr Cys Cys Gln Leu Ser Glu Glu Lys
    450                 455                 460

Trp Ser Gly Cys Gly Glu Gly Met Ala Asp Ile Phe Ile Gly His Leu
465                 470                 475                 480

Cys Ile Arg Asn Glu Ala Ser Pro Val Asn Ser Gly Ile Ser His Cys
                485                 490                 495

Cys Asn Ser Ser Tyr Ser Asn Arg Arg Leu Cys Ile Thr Ser Phe Leu
            500                 505                 510

Arg Asp Glu Thr Tyr Ala Pro Pro Pro Phe Ser Glu Asp Lys Phe Ile
        515                 520                 525

Phe His Lys Asp Leu Cys Gln Ala Gln Gly Lys Ala Leu Gln Thr Met
    530                 535                 540

Lys Gln Glu Leu Leu Ile Asn Leu Val Lys Gln Lys Pro Glu Leu Thr
545                 550                 555                 560

Glu Glu Gln Leu Ala Ala Val Thr Ala Asp Phe Ser Gly Leu Leu Glu
                565                 570                 575

Lys Cys Cys Lys Ala Gln Asp Gln Glu Val Cys Phe Thr Glu Glu Gly
            580                 585                 590

Pro Lys Leu Ile Ser Lys Thr Arg Asp Ala Leu Gly Val
        595                 600                 605
```